United States Patent [19]

Molbert et al.

[11] Patent Number: 4,525,854
[45] Date of Patent: Jun. 25, 1985

[54] RADIATION SCATTER APPARATUS AND METHOD

[75] Inventors: John L. Molbert; Eddie R. Riddle, both of Durham, N.C.

[73] Assignee: Troxler Electronic Laboratories, Inc., Research Triangle Park, N.C.

[21] Appl. No.: 477,820

[22] Filed: Mar. 22, 1983

[51] Int. Cl.³ .................. G01N 23/00; G01T 1/16; G01V 5/00; H01J 39/00
[52] U.S. Cl. ................................. 378/089; 250/266
[58] Field of Search ............ 378/89, 87, 5, 6, 54, 378/51, 55, 56, 90; 250/266

[56] References Cited

U.S. PATENT DOCUMENTS

| | | | |
|---|---|---|---|
| 2,997,586 | 8/1961 | Scherbatskoy | 378/89 |
| 3,148,279 | 9/1964 | Skala | 378/89 |
| 3,202,822 | 8/1965 | Kehler | 250/266 |
| 3,840,746 | 10/1974 | Kehler | 378/89 |
| 4,123,654 | 10/1978 | Reiss et al. | 378/89 |
| 4,297,575 | 10/1981 | Smith et al. | 250/266 |

Primary Examiner—Alfred E. Smith
Assistant Examiner—T. N. Grigsby
Attorney, Agent, or Firm—Bell, Seltzer, Park & Gibson

[57] ABSTRACT

A radiation scatter gauge includes multiple detector locations for developing separate and independent sets of data from which multiple physical characteristics of a thin material and underlying substrate may be determined. In an illustrated embodiment, the apparatus and method of the invention are directed to determining characteristics of resurfaced pavement by nondestructive testing. More particularly, the density and thickness of a thin asphalt overlay and the density of the underlying pavement may be determined.

18 Claims, 10 Drawing Figures

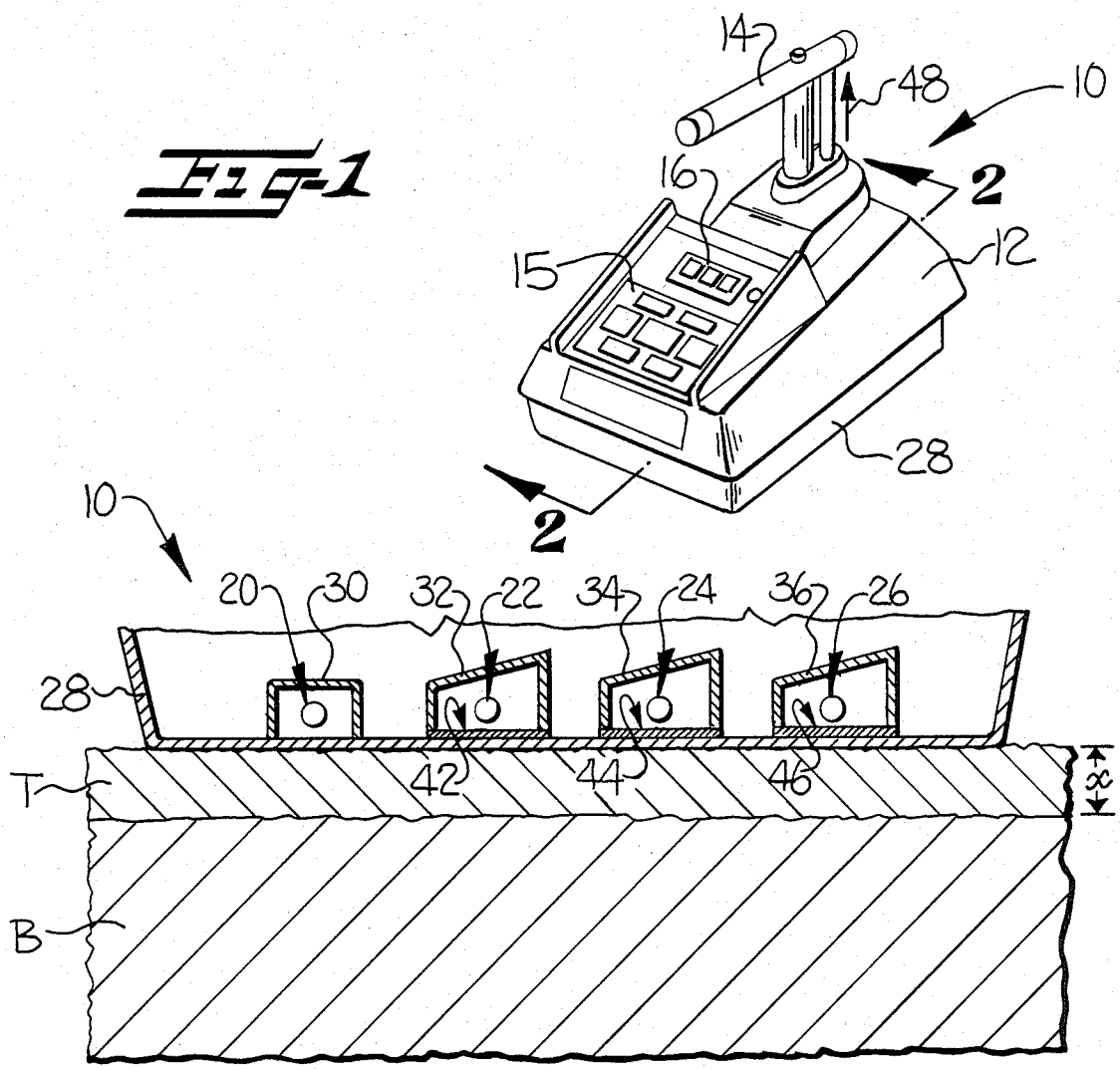
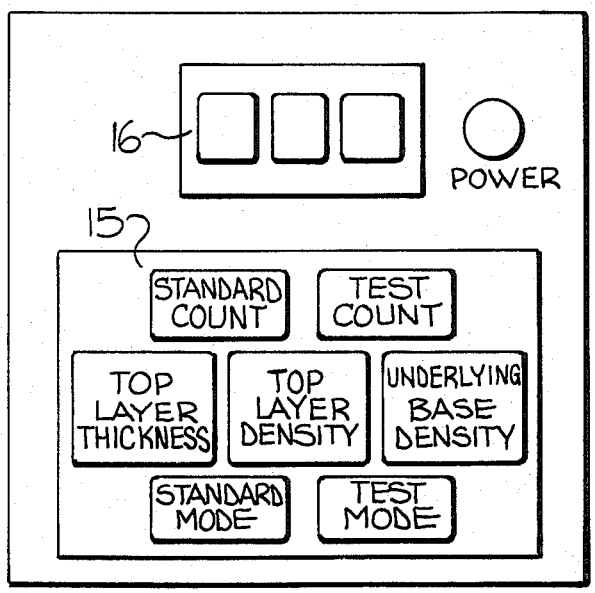

RADIATION SCATTER APPARATUS AND METHOD

BACKGROUND OF THE INVENTION

1. Field of the Invention

The present invention relates to apparatus and methods for determining physical characteristics of test materials. More particularly, the invention relates to apparatus and methods for determining physical characteristics relating to relatively thin test materials, for example, density and thickness characteristics thereof.

2. Description of the Prior Art

Nuclear radiation gauges for determining density and moisture characteristics of soil and asphaltic materials are well known. One example of such a gauge is described in U.S. Pat. No. 2,781,453. Such gauges employ the phenomenon of Compton scattering of gamma rays and are known by those skilled in the art as "scatter" gauges.

Gauges currently in use for measuring the density of soil, asphalt and other materials are most effective at measuring densities of materials over depths of approximately 4 to 6 inches. When the thickness of the test material is at least 4 to 6 inches, the prior gauges have been highly successful. However, increasing difficulty is encountered as the thickness of the test material decreases.

With the increasing cost of paving materials, the practice in maintaining and resufracing paved roadbeds has become one of applying overlays down to thicknesses on the order of one inch. With lifts of such a thickness range, prior density gauges are ineffective for measuring the density of the overlay applied. More particularly, such gauges are not capable of directly measuring the density of layers having a thickness of less than about four inches. The problem arises due to the depth of penetration of gamma rays. The gauge "sees" through the thin overlay so that the underlying pavement substantially influences the gauge reading.

Recognizing this limitation on the prior density gauges, efforts were made in the mid 1970's to establish a procedure for determining the density of thin overlays utilizing then existing gauges. A nomograph was developed that allowed approximation of the overlay density. However, in order to obtain the density of the overlay by the nomograph technique, it became necessary to know both the density of the underlying base and the thickness of the overlay. The technique was as follows. First, the operator determined the base density by taking nuclear density tests of the existing roadbed. Second, after the overlay pavement was applied and compacted, the overlay thickness was determined by taking a core sample, or like operation. Third, density tests were performed on top of the overlay to generate data. With the density measurement from the first test, the overlay thickness measurement and the density data from the second test, the density of the overlay could be approximated by reference to a nomograph.

A drawback of the prior art nomograph technique is that the underlying pavement is further compacted when the overlay is compacted, thereby introducing an inconsistency between the gauge reading of the underlying pavement density and its actual density after application of the overlay. Furthermore, it has proven difficult to take the second density reading (after the overlay is applied) at precisely the same location as the first reading. Lastly, the thickness of the overlay may vary between the sample location and the location where the nuclear gauge is placed for testing. In addition to the above problems, and perhaps most importantly, the nomograph technique required multiple steps, both before and after application of the overlay, as well as a destructive thickness measurement of the overlay.

SUMMARY OF THE INVENTION

In accordance with the present invention there are provided radiation scatter methods and apparatus for determining multiple physical characteristics relating to a relatively thin material and any underlying substrate material that is present.

While the present invention is not limited to types of test materials or the determination of any particular set of physical characteristics, the invention has been used in connection with thin overlays applied in pavement maintenance or resurfacing operations to determine (i) the density of the overlay, (ii) the thickness of the overlay, and (iii) the density of the underlying pavement base. The foregoing characteristics may be determined in a single nondestructive test.

In one aspect of the invention, the apparatus comprises a radiation source for emitting radiation into a relatively thin material and any substrate material that is present, and detector means for obtaining separate and distinct measurements of scattered radiation at a plurality of detector locations. The separate and distinct radiation measurements are weighted toward the physical characteristics as they exist at different depths in the thin material and substrate and provide independent data that, when simultaneously interrelated with derived mathematical relationships, serve collectively to determine values for the physical characteristics. The apparatus may include a microprocessor that incorporates a fixed set of instructions for determining values for the physical characteristics.

More particularly, the radiation measurements may be detected by a plurality of radiation detectors located in predetermined spaced relation to the source of radiation, with each detector being so positioned and having filtering characteristics so as to receive radiation counts distinctive from the counts received by the other detectors. Recording means may be operatively associated with the detectors for separately recording measured radiation information from each detector. Information storage means stores the empirically derived mathematical equations, each equation relating the recorded radiation information to the unknown values for the physical characteristics. The microprocessor may simultaneously solve the equations to derive the values.

The foregoing apparatus, when used in association with thin overlays applied in pavement resurfacing operations, may include a housing enclosing a source of gamma radiation and three coplanar radiation detectors that provide three independent total radiation counts. Each count may be weighted toward different radiation energy levels due to the detectors' differing filtering characteristics and positioning. Thus, the three independently derived total radiation counts, when substituted into three empirically derived mathematical equations (each having three unknowns), enable all three unknowns to be calculated by simultaneously solving the equations.

The method of the invention, in one aspect, includes the steps of directing radiation into a thin material and any substrate material that is present, and obtaining separate and distinct measurements of scattered radiation that are weighted toward the physical characteristics as they exist at different depths of the thin material and substrate, the measurements providing independent data that collectively determine values for at least two physical characteristics relating to the thin material.

In a particular method of practicing the invention, the radiation is directed from a single source and the measurements are obtained at different distances from the source. According to other methods, the radiation is directed from multiple sources. When there are multiple sources, the measurements may be obtained at a single point.

The measurements may be taken in the form of radiation count information, such as total radiation counts or radiation count rates, or in other forms appropriate for the particular application.

BRIEF DESCRIPTION OF THE DRAWINGS

The invention will be more fully understood from the following detailed description thereof taken in connection with the accompanying drawings, in which—

FIG. 1 is a perspective view of a radiation gauge constructed in accordance with the present invention;

FIG. 2 is an enlarged, partly schematic, sectional view through the lower portion of the gauge illustrated in FIG. 1 as taken substantially along line 2—2 of FIG. 1, with the gauge resting upon a test material;

FIG. 3 is a plan view of the display of the gauge illustrated in FIG. 1;

DETAILED DESCRIPTION OF THE INVENTION

Figure 4:
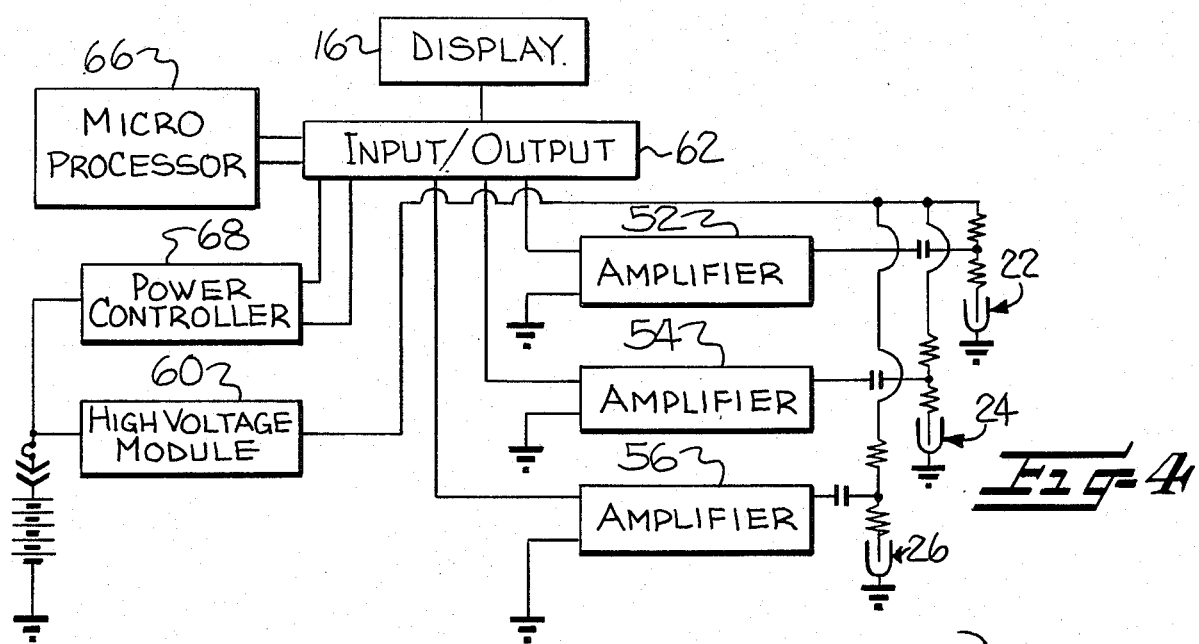
FIG. 4 is a schematic diagram of certain circuit components of the gauge illustrated in FIGS. 1, 2 and 3.

While the present invention will be described hereinafter with particular reference to the accompanying drawings, it is to be understood at the outset of the description which follows that it is contemplated that the present invention may be varied in specific detail while still achieving the desirable characteristics and features of the present invention. Accordingly, the description is to be understood as a broad enabling teaching directed to persons skilled in the applicable arts, and is not to be understood as restrictive.

Referring to the drawings, there is shown a radiation scatter apparatus 10 constructed in accordance with the present invention.

Apparatus 10 includes a housing generally indicated at 12 in FIG. 1, a handle 14, a keyboard 15 and a display 16. Housing 12 encloses a suitable radiation source 20 (FIG. 2) and a series of three detectors 22, 24, 26. The radiation source may be a CS-137 source of gamma radiation and the detectors may take the form of Geiger-Mueller tubes sensitive to photons. The source 20 and detectors 22, 24, 26 may be mounted in an appropriate manner in or to a pan 28 forming a planar bottom surface of housing 12. Shielding of the source and detectors about their respective sides and tops are achieved by appropriate radiation shields indicated at 30, 32, 34, 36. This shielding prevents an appreciable amount of radiation from reaching the detectors in a path direct from the source.

Detectors 22, 24, 26 are provided with underlying radiation filters 42, 44, 46. As explained in more detail below, the filters are formed from materials that modify the energy spectrum and intensity of radiation incident on them.

In FIG. 2 the radiation source 20 is shown in its lowered position proximate to the bottom surface of the housing for supplying a somewhat collimated emission of radiation into a thin material T and underlying base B. In this position source 20 is substantially coplanar with detectors 22, 24, 26. As well known to those skilled in the art, the source may be withdrawn to a fully enclosed and shielded position by retraction of handle 14 in the direction of arrow 48 in FIG. 1.

Prior to further discussion of the structure and operation of apparatus 10, it will be helpful to review some of the underlying principles of nuclear density gauge operation and geometry, particularly as applied to multiple layer test materials.

As a general rule, the amount of radiation reaching the single detector system of a prior art nuclear density gauge decreases exponentially with increasing density of the test material. This relationship follows a standard attenuation equation throughout the usable density range of the gauge. One well known form of the attenuation equation is $$CR = A \exp(-BD_G) - C$$

CR = count ratio;

$D_G$ = density calculated by the gauge;

A, C = constants primarily dependent on gauge geometry; and

B = constant primarily dependent on mass attenuation coefficient and gauge geometry.

(In order to eliminate long term effects of source decay and electronic drift, it is customary practice for all data to be normalized to a standard reference count and expressed as a ratio, the "count ratio".)

As mentioned above in connection with the Description of the Prior Art, prior nuclear density gauges optimally measure densities over a depth range of approximately four to six inches in tests of soil, asphalt or other materials. The usual application of these gauges is with single layer, substantially homogeneous materials, for example asphalt pavement having a thickness of four inches or more. With layers of less than about four inches, the gauge "sees" through the top layer so that the gauge reading is influenced by the underlying substance.

Figure 5A:
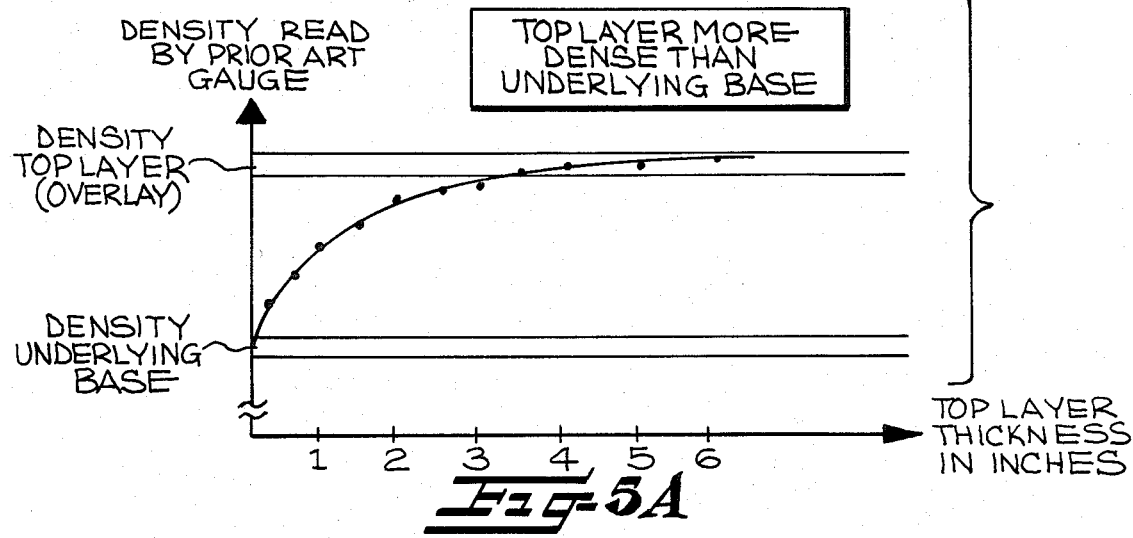
FIG. 5A is a graph relating prior art density gauge readings as a function of top layer thickness in a situation where the gauge has been placed upon two layer test materials of varying top layer thicknesses, with the top layer being more dense than the underlying base substance.
Figure 5B:
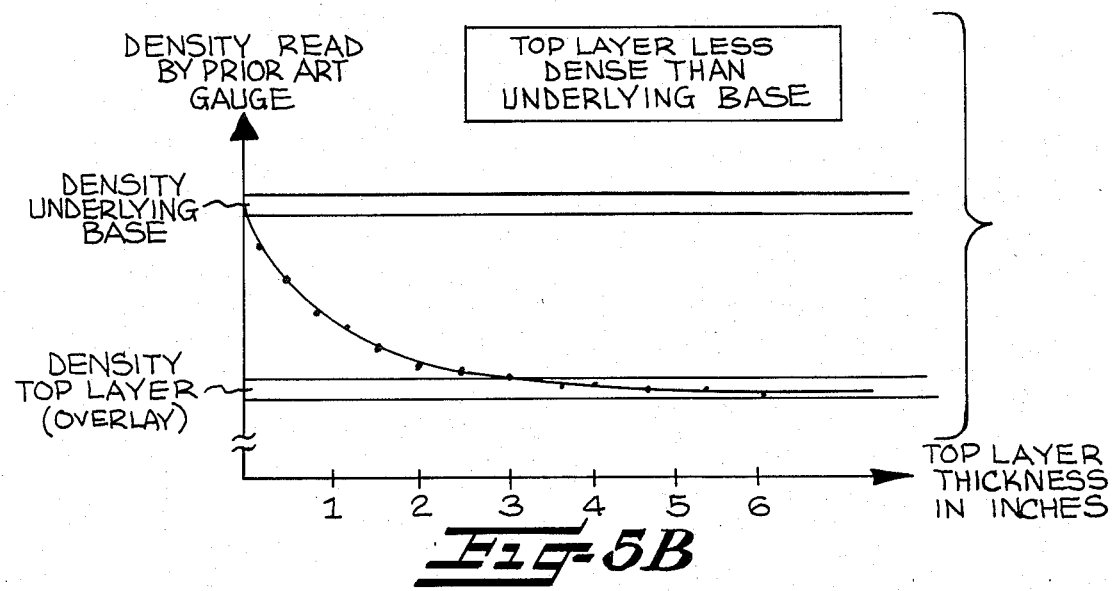
FIG. 5B is a graph similar to that shown in FIG. 5A except that the top layer is less dense than the underlying base substance.

The influence of the underlying base layer on the density reading is best shown by the graphs of FIGS. 5A and 5B. These graphs were developed by taking density readings with a prior art, single detector gauge that was placed over two-layer test pieces, with the layers being homogeneous substances of different densities. The graphs illustrate that when the top layer has a thickness of about four inches or more, the gauge essentially reads the density of the top layer. However, as the top layer thickness decreases to less than about four inches the underlying base material influences the density reading of the gauge to a point where, as expected, with a top layer thickness of zero the gauge reads the density of the underlying base material.

It is clear from the data contained in FIGS. 5A and 5B that in situations where the top layer is less than about four inches, the density of the underlying base material has a significant impact on the gauge density reading ($D_G$).

The curves of FIGS. 5A and 5B represent situations where the density of the top layer ($D_T$) and the density of the underlying base ($D_B$) are held constant at different values while the thickness of the top layer (X) varies in the range from 0 to 6 inches. Thus, the curves of FIGS. 5A and 5B are two dimensional since $D_T$ and $D_B$ are known and held constant. However, the values of $D_T$ and $D_B$ can be varied in general application such that there are three variables, $D_T$, X and $D_B$. By the selection of an appropriate form of equation and appropriate curve fitting constants, the general function may be expressed as a derived equation that is unique to the particular gauge, namely:

$$D_G = f(D_T, X, D_B).$$

This equation may take any number of different forms that may be derived by one of skill in the art.

It has been determined that the geometrical relationship between a radiation source and a detector has a significant impact on what is seen by the detector. While the geometrical relationship may be varied by changing the angular relationship of the radiation beam with respect to the detector, or by other changes, the geometrical relationship may be varied most easily by varying the distance between the source and detector. What has been found is that the amount of radiation reaching the detector decreases exponentially with increase in the source-to-detector distance. Further, as source-to-detector distance decreases, the reading of the gauge is more heavily weighted toward the density of the material close to the surface. Conversely, at larger source-to-detector distances, the gauge reading becomes more of an average density over the approximately four inch depth seen by the gauge. As pointed out below, this phenomenon enables detectors placed at different distances from the source to make separate and distinct radiation measurements that are independent of each other. These independent radiation measurements reflect physical characteristics of the same material, but are weighted more heavily toward different depth strata within the material.

It has also been determined that the radiation measurements of a detector are significantly affected by the imposition of a radiation filter between the souce and the detector, with the filter most commonly being placed in proximity to the detector as exemplified by filters 42, 44, 46 shown in FIG. 2. When used in conjunction with gamma radiation, the filters may take the form of thin layers of elements such as lead, zinc and cadmium. By selection of filters formed from these different materials, or formed by differing thicknesses of the materials, scattered photons may be attenuated before reaching the detector.

It has been determined that radiation scattered from greater depths, for example up to about three to five inches, will, on average, return to the detectors at a lower energy level than the radiation that has passed a lesser distance into a test piece. Thus, by the imposition of a filter with a relatively high filtering effect, most of the scattered radiation from below particular depths may be effectively filtered from the respective detector resulting in that detector being more heavily weighted in what it "sees" by the physical characteristics of the material closer to the detector. Conversely, by the imposition of a very low filtering effect the detector will see proportionally more of the radiation scattered from greater depths so that such a detector is not so heavily weighted toward the physical characteristics near the surface of the test material.

As explained in detail below, the present invention recognizes that, by appropriate selection of the geometric positioning of detectors and the filtering characteristics associated with the detectors, a gauge may be constructed with multiple detectors that act independently to obtain radiation measurements distinctive from the measurements obtained by the other detectors. Each independent measurement has a different significance from the measurements of the other detectors. Referring to FIG. 2, the single radiation source 20 and three detectors 22, 24, 26 of apparatus 10 provide, in effect, the capability of generating three independent and discrete sets of radiation data which collectively determine values for the physical characteristics under test. While the radiation measurements are made by accumulating counts in the preferred embodiment of the invention, other forms of measurement of scattered radiation may be used.

Each of the three independent detectors of apparatus 10 may measure radiation scattered from two-layer test materials to provide three separate equations that relate gauge density ($D_G$) to the density of a top layer ($D_T$), the thickness of a top layer (X) and the density of an underlying base ($D_B$), as follows:

$$D_{G1} = f_1(D_T, X, D_B)$$

$$D_{G2} = f_2(D_T, X, D_B)$$

$$D_{G3} = f_3(D_T, X, D_B).$$

These three equations may be substituted into the standard calibration equations ($CR = A \exp(-BD_G) - C$) for each system to provide the following three equations:

$$CR_1 = A_1 \exp[-B_1(f_1(D_T, X, D_B))] - C_1$$

$$CR_2 = A_2 \exp[-B_2(f_2(C_T, X, D_B))] - C_2$$

$$CR_3 = A_3 \exp[-B_3(f_3(D_T, X, D_B))] - C_3$$

These three equations, when solved simultaneously, yield values for the three physical characteristics, $D_T$, X and $D_B$.

It will be appreciated that if each detector 22, 24, 26 were to "see" the scattered radiation in essentially the same fashion, the radiation measurement information from each detector would be substantially the same and the functions relating them to the three unknown values would, likewise, be substantially the same.

However, in accordance with the present invention, the detectors are provided with a combination of geometrical positioning and filtering characteristics so that they "see" the thin material and substrate in substantially different fashions; i.e., they "see" different scattered radiation profiles. Thus, their radiation measurement information is distinct by being weighted toward different depth strata of the thin material and substrate. By experimentation with different combinations of detector positioning and filtering characteristics, it is possible to develop three independent and quite different detector systems that enable the functions to sufficiently differentiate so that the three equations may be simultaneously solved to give meaningful values for the three unknowns. Of course, where the material being tested has substantially the same density over a depth range of about 4 to 6 inches or more, the gauge will see the same density characteristics over the entire depth and the radiation measurements will so indicate.

Figure 6:
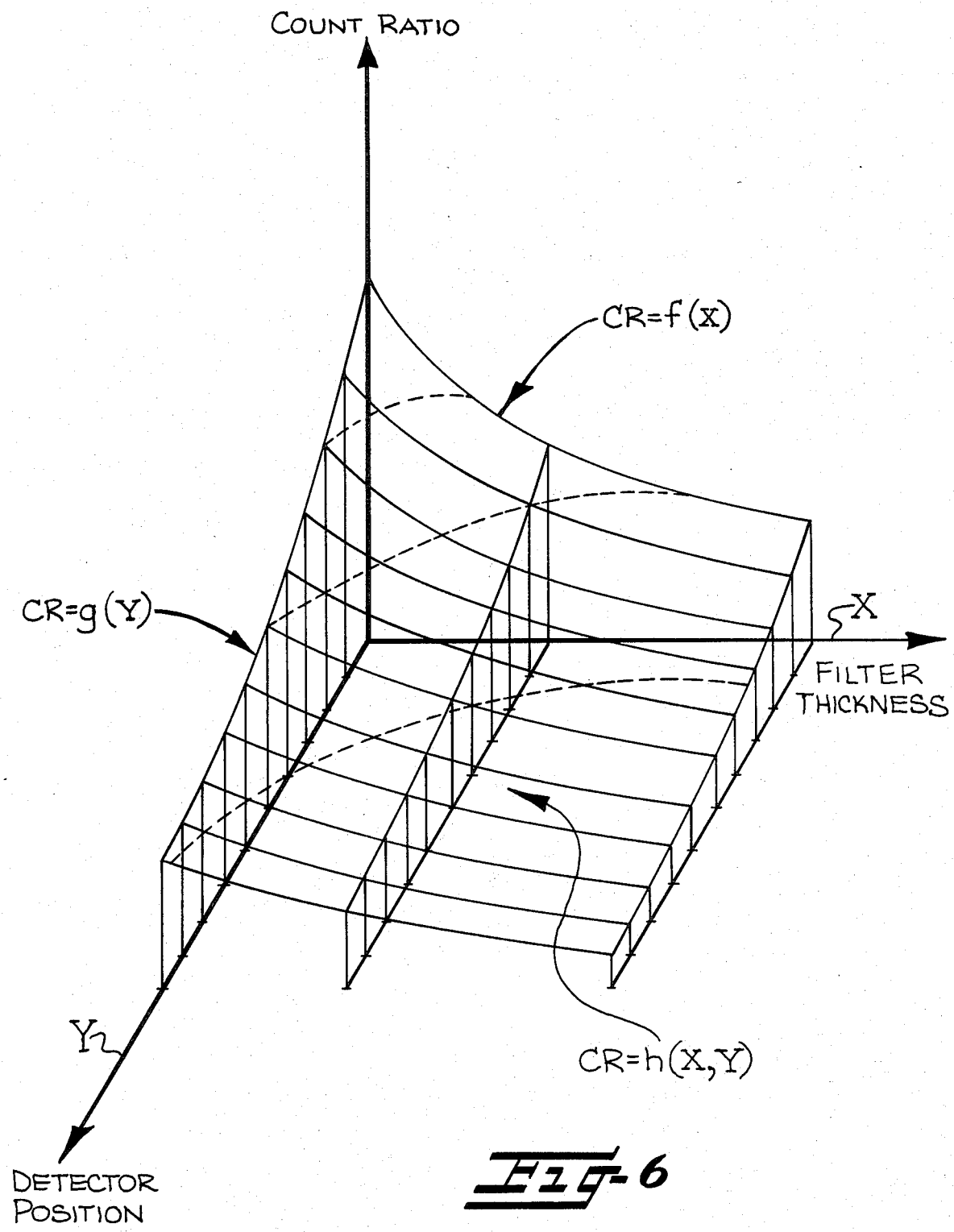
FIG. 6 is a three dimensional graph showing the manner in which the radiation counts measured by a detector vary as a function of (1) filter thickness and (2) detector position, with the developed three dimensional surface representing radiation counts as a function of both variables.

The three dimensional graph of FIG. 6 dramatically illustrates the independent effects of filter thickness and source-to-detector positioning on the count ratio. The three detector systems of apparatus 10 may be so constructed as to take full advantage of the phenomena illustrated by the graph.

It will be appreciated that the particular empirically derived equations that are achieved by selecting an equation form and appropriate constants (preferably derived from curve fitting routines) are subject to many different forms. The selection of the constants and forms of the equations may be achieved by one of skill in the relevant art.

It will also be appreciated that the use herein of the term "thin material", and equivalent terms, relates to materials thin enough so that some appreciable portion of the radiation may pass therethrough and be subject to scattering back from any substrate material that is present. In this regard, it will be noted that the present invention may have application to situations where a thin material stands alone without a substrate per se, or where the radiation, after passing through the thin material, passes into a gas or liquid on the opposite side of the thin material. In certain applications of the invention where the density of the substance on the opposite side of the thin layer is known—even if it is only air or water—that information may be useful in calculating density and thickness values for the thin material.

While the specification refers to an "underlying substrate material" to facilitate the description of the invention, it will be appreciated that this term and like terms are intended to encompass any situation where a second substance lies beneath or beyond the "thin material", i.e., on the other side of the thin material from the source and detector(s).

In the gauge illustrated in FIGS. 1, 2 and 4 each of the detectors 22, 24, 26 is electrically connected with a corresponding amplifier 52, 54, 56. Additionally, as is required, the detectors are connected with a source 60 of high voltage. Outputs from the amplifiers 52, 54, 56 are directed to an input/output circuit generally indicated at 62 and are available through such circuitry to an electronic computing device in the form of a microprocessor 66 and to display 16. Power to the entire device is supplied by a power controller 68.

The microprocessor performs in the circuit of the present invention (as schematically illustrated in FIG. 4) a number of functions including governing time intervals for gauging in both "standard" and "measure" modes. The microprocessor also serves the function of a recorder operatively associated with the detectors for separately recording the measured radiation information from each detector. In this regard, the radiation information preferably takes the form of a total radiation count for each Geiger-Mueller detector per time interval. In other embodiments the radiation information may take other forms, such as radiation count rates.

The microprocessor also serves to store, in appropriate form, the three empirically derived mathematical equations that functionally relate the radiation measurements (e.g., total radiation count information) to the values for the density and thickness characteristics. Further, the microprocessor simultaneously solves the mentioned equations to calculate the values. Other functions, generally known to persons appropriately skilled in the art, are performed by the microprocessor.

With reference to FIG. 3, in operation apparatus 10 may be initially placed in the "standard" mode to take a standard count on a reference standard in the manner well known to those skilled in the art. Once the standard count information is stored in the microprocessor the gauge may be placed in the "measure" mode to take test counts on an appropriate test material, for example resurfaced pavement including a thin overlay and an underlying pavement base. Through appropriate circuitry the values for the unknowns may be calculated by reference of the test count information to the standard counts. Overlay thickness, overlay density and underlying base density may be disclosed, for example at display 16.

Apparatus 10 may be provided with the capability of calculating values for two of the three density and thickness characteristics where one of the values is known. To this end, the apparatus may include means for entering a known value, for example, thickness of the overlay. Where the operator can always independently determine one of the variables, the apparatus may be constructed with a minimum of two detector locations—with the known value being entered prior to calculation.

Figure 7:
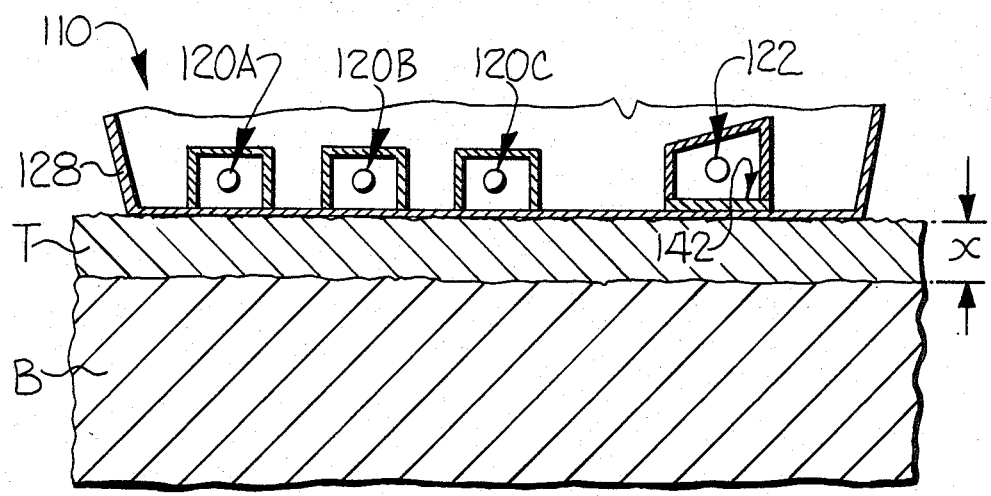
FIG. 7 is a sectional view through the lower portion of an alternative embodiment gauge having multiple radiation sources and a single detector.

FIG. 7 illustrates a portion of an alternative embodiment gauge 110 having a pan 128, three radiation sources 120A, 120B, 120C and a single detector 122 with associated filter 142. By sequentially activating the multiple sources, alone or in various combinations, the single detector may make multiple measurements of scattered radiation that are weighted toward the physical characteristics as they exist at different depths in the thin material and substrate.

Figure 8:
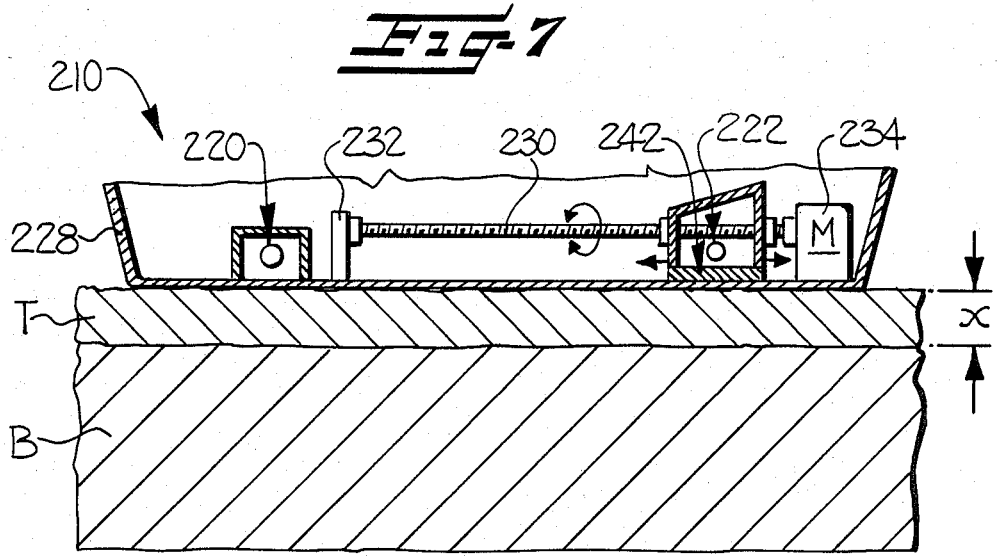
FIG. 8 is a sectional view through the lower portion of a second alternative embodiment gauge having a detector mounted for movement relative to the source.

FIG. 8 illustrates a portion of a second alternative embodiment gauge 210 having a pan 228, a source 220 and a detector 222 and associated filter 242 that are movable with respect to the source. As shown, detector 222 is mounted for reciprocating motion on a threaded member 230 that is journalled at one end by journal 232 and is rotatably driven at the other end by a motor 234. Thus, the source-to-detector distance may be varied by actuation of motor 234 so that measurements of scattered radiation may be made at different detector locations along the path of detector 222.

Figure 9:
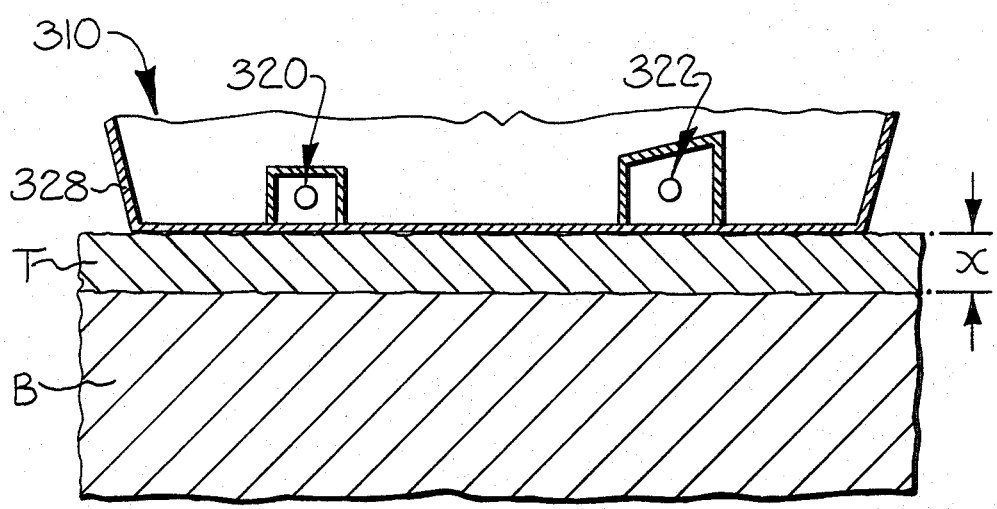
FIG. 9 is a sectional view through the lower portion of yet another alternative embodiment gauge having a source and a detector with multiple radiation energy discriminating capabilities.

FIG. 9 illustrates yet another alternative embodiment gauge 310 including a pan 328, a source 320 and a detector 322 having multiple radiation energy discriminating capabilities. Detector 322 may take the form of a sodium iodide crystal detector that can be placed in several modes of operation to measure incident scattered radiation at several different energy level bands. The several measurements so made provide multiple measurements that are appropriately weighted toward the physical characteristics as they exist at different depths in the thin material and substrate.

While the present invention has been described in connection with illustrated embodiments, it will be appreciated that modification may be made without departing from the true spirit and scope of the invention. For example, the radiation source may emit other forms of radiation, such as neutron radiation for the detection of moisture and other characteristics of test materials. This and other modifications are intended to fall within the true scope of the invention.

What is claimed is:

1. A radiation scatter apparatus for use in association with a relatively thin overlay material overlying a substrate material to measure the density of the overlay material, the thickness of the overlay material, and the density of the substrate material, said apparatus comprising:
   source means for emitting gamma radiation into the overlay material and the substrate material;
   detector means including at least three radiation detectors located in predetermined spaced relation to said source for detecting scattered radiation, each detector being so positioned and having such filtering characteristics so as to measure radiation distinctive from the radiation measured by the other detectors; and
   recording means operatively associated with said detector means for separately recording measured radiation information from each said detector for use with derived mathematical relations to determine the density of the overlay material, the thickness of the overlay material, and the density of the substrate material.

2. An apparatus as set forth in claim 1 further comprising:
   information storage means for storing at least three derived mathematical equations relating the recorded radiation information to the density of the overlay material, the thickness of the overlay material, and the density of the substrate material;
   means for solving the mentioned equations to derive values for the density of the overlay material, the thickness of the overlay material, and the density of the substrate material; and
   means for disclosing the derived values.

3. An apparatus as set forth in claim 1 wherein the recorded radiation information is in the form of count rates.

4. A radiation scatter apparatus useful for nondestructively testing an overlay applied in a pavement maintenance or resurfacing operation to determine the following three physical characteristics: (i) the density of the overlay, (ii) the thickness of the overlay, and (iii) the density of the pavement base directly under the overlay, said apparatus comprising:
   a housing having a planar bottom surface;
   a source of gamma radiation contained within said housing, said source being positionable to a location proximate to the housing bottom surface to emit gamma radiation into the overlay and underlying pavement base when the apparatus is placed on an overlay;
   at least three radiation detectors mounted within said housing for measuring profiles of scattered radiation, said detectors being located proximate to the housing bottom surface and at different distances from said source so that the radiation profile measured by each detector is separate and distinct from the radiation profiles measured by the others detectors; and
   recording means operatively associated with said detectors for separately recording measured radiation information from each said detector.

5. An apparatus as set forth in claim 4 including filter means associated with at least certain ones of said detectors for modifying the incident energy spectrum of scattered radiation.

6. An apparatus as set forth in claim 4 including means for entering a known value of one of the physical characteristics (i), (ii), and (iii) and for using the known value in determining values of the other two characteristics.

7. An apparatus as set forth in claim 4 wherein said detectors are three in number for generating three separate and distinct accumulated counts of scattered radiation, and wherein the three accumulated counts are related to three derived mathematical relationships that are solved simultaneously to give values for the three physical characteristics (i), (ii) and (iii).

8. An apparatus as set forth in claim 4 further comprising:
   information storage means for storing at least three derived mathematical equations relating the recorded information to (i) the density of the overlay, (ii) the thickness of the overlay, and (iii) the density of the underlying pavement base;
   means for solving the mentioned equations to determine values for (i), (ii) and (iii) above; and
   means for disclosing the derived values.

9. An apparatus as claimed in claim 8 wherein the recorded information is in the form of total radiation counts.

10. A method of testing an overlay applied in a pavement maintenance or resurfacing operation to determine values for the following three physical characteristics: (i) the density of the overlay, (ii) the thickness of the overlay, and (iii) the density of the pavement base directly under the overlay, said method comprising the steps of:
    placing a nuclear gauge over the overlay;
    directing gamma radiation from a source in the gauge into the overlay and pavement base;
    detecting scattered radiation counts at at least three detection points inside the gauge;
    separately recording the radiation count information from each detection point; and
    calculating values for the physical characteristics (i), (ii) and (iii) by solving three derived simultaneous equations, each of which functionally relates the count information associated with a respective detection point to the three values.

11. A method as set forth in claim 10 wherein the recording and calculating steps are performed by an electronic computing device that incorporates a fixed set of instructions functionally corresponding to the three mentioned equations.

12. A method of measuring the density and thickness of an overlay applied in a pavement maintenance or resurfacing operation, said method comprising the steps of:
- obtaining a value for the density of the pavement base that is directly under the overlay;
- directing gamma radiation from a source into the overlay and pavement base;
- detecting radiation scattered therefrom with at least two detectors, each detector being so positioned and having such filtering characteristics as to measure radiation distinctive from the radiation measured by any other detector;
- simultaneously solving at least two derived mathematical equations, each equation relating one of the radiation measurements to the density of the pavement base and the two unknown values for the density and thickness of the overlay; and
- disclosing the calculated values.

13. A method as set forth in claim 12 wherein the values are calculated by an electronic calculating device and including the steps of entering the value of the pavement base density into the device, entering the radiation measurements into the device and simultaneously solving the equations by the device.

14. A method of testing a relatively thin material to derive values for the density of the thin material, the thickness of the thin material and the density of a substrate material underlying the thin material, said method comprising:
- directing nuclear radiation from a source into the thin material and the substrate material;
- detecting radiation scattered therefrom with at least three spaced detectors, each detector being so positioned and having such filtering characteristics as to measure radiation distinctive from the radiation measured by the other detectors; and
- determining the three mentioned values by solving at least three simultaneous mathematical equations, each equation relating one of the radiation measurements to the three values.

15. A method of testing an overlay applied in a pavement maintenance or resurfacing operation to determine values for two of the following physical characteristics: (i) the density of the overlay, (ii) the thickness of the overlay, and (iii) the density of the pavement base directly under the overlay, where the value for one of the three characteristics is already known, said method comprising the steps of:
- directing gamma radiation from a source into the overlay and the pavement base;
- making at least two measurements of scattered radiation at at least two detector locations that are in predetermined geometrical relation with respect to the source;
- recording the measurements in an electronic computing device to provide discrete sets of data corresponding to the respective detector locations;
- entering the known value for one of the three characteristics in the electronic computing device; and
- calculating the two unknown values by simultaneously solving at least two derived equations, each of which functionally relates one of the discrete sets of data to the two unknown values and the one known value.

16. A radiation scatter apparatus useful for nondestructively testing an overlay applied in a pavement maintenance or resurfacing operation to determine values for two of the following physical characteristics: (i) the density of the overlay, (ii) the thickness of the overlay, and (iii) the density of the pavement base directly under the overlay, where the value for one of the three characteristics is already known, said apparatus comprising:
- a housing having a bottom surface;
- a source of gamma radiation contained within said housing, said source being positionable to a location proximate to the housing bottom surface to emit gamma radiation into the overlay and underlying pavement base when the apparatus is placed on an overlay;
- at least two radiation detectors mounted within said housing in predetermined geometrical relation with respect to the source for making respective measurements of scattered radiation; and
- electronic computing means cooperating with said detectors, said computing means including means for recording the measurements from said at least two detector locations as respective discrete sets of data corresponding to the respective detector locations, means for entering the known value for one of the three characteristics, and means for calculating the two unknown values by solving at least two derived equations, each of which functionally relates one of the discrete sets of data to the two unknown values and the one known value.

17. An apparatus for measuring the density and thickness of an overlay applied in a pavement maintenance or resurfacing operation, said apparatus comprising:
- a housing having a bottom surface;
- a source of gamma radiation contained within said housing for emitting gamma radiation into the overlay and underlying pavement base when the apparatus is placed on an overlay;
- at least two radiation detectors mounted within said housing for measuring profiles of scattered radiation, each detector being so positioned and having such filtering characteristics as to measure radiation distinctive from radiation measured by any other detector; and
- electronic computing means operatively associated with said detectors, said computing means including means for solving at least two derived mathematical equations, each equation relating one of the radiation measurements to the density of the pavement base and the two unknown values for the density and thickness of the overlay, and
- means for disclosing the calculated values.

18. A radiation scatter apparatus useful for nondestructively testing an overlay applied in a pavement maintenance or resurfacing operation to determine the density of the overlay, where the thickness of the overlay is already known, said apparatus comprising:
- a housing having a bottom surface;
- a source of gamma radiation contained within said housing, said source being positionable to a location proximate to the housing bottom surface to emit gamma radiation into the overlay and underlying pavement base when the apparatus is placed on an overlay;
- at least two radiation detectors mounted within said housing in predetermined geometrical relation with respect to the source for making respective measurements of scattered radiation; and
- electronic computing means cooperating with said detectors, said computing means including means for recording the measurements from said at least two detector locations as respective discrete sets of data corresponding to the respective detector locations, means for entering the known thickness of the overlay, and means for calculating the density of the overlay by solving at least two derived equations, each of which functionally relates one of the discrete sets of data to the density of the overlay, the density of the pavement base directly under the overlay, and the thickness of the overlay.

* * * * *